United States Patent [19]

Jauw

[11] Patent Number: 4,950,653

[45] Date of Patent: Aug. 21, 1990

[54] SOLID IODOPHOR COMPOSITION

[75] Inventor: Tjoe H. Jauw, Amsterdam, Netherlands

[73] Assignee: Euroceltique, S.A., Luxembourg

[21] Appl. No.: 85,634

[22] Filed: Aug. 10, 1987

[30] Foreign Application Priority Data

Sep. 12, 1986 [GB] United Kingdom ................ 8622012

[51] Int. Cl.$^5$ ............................................ A61K 31/00
[52] U.S. Cl. ...................................... 514/53; 424/80; 424/672; 424/667; 514/54; 514/61
[58] Field of Search ............... 514/53, 54, 61; 424/80, 424/150, 672, 667

[56] References Cited

U.S. PATENT DOCUMENTS

| 4,010,259 | 3/1977 | Johansson | 514/53 |
| 4,344,930 | 8/1982 | MacRae et al. | 424/81 |
| 4,576,818 | 3/1986 | Shetty | 424/150 |
| 4,668,510 | 5/1987 | Shetty | 424/150 |
| 4,755,378 | 7/1988 | Buxton et al. | 424/80 |

Primary Examiner—Ronald W. Griffin
Assistant Examiner—Everett White
Attorney, Agent, or Firm—Steinberg & Raskin

[57] ABSTRACT

A solid iodophor composition contains a water-soluble iodophor, especially povidone iodine, and at least one of a urea and a sugar alcohol, especially mannitol, sorbitol or xylitol. The composition may also contain a sugar such as sucrose or lactose.

The advantage claimed in the ready solublility of the composition in water. This would allow the supply of iodophors in solid, rather than liquid, form.

15 Claims, No Drawings

SOLID IODOPHOR COMPOSITION

The present invention relates to a solid idophor composition and, in particular, to a solid iodophor compositoin that is readily soluble in water.

Iodophors are physiologically acceptable complexes of iodine with organic polymers, in which the germicidal and microbiocidal activity of elemental iodine is maintained. In the main, they are water-soluble.

Amongst the most effective (microbiocidally) of these iodophors are the complexes of iodine with non-ionic, non-detergent (non-surface active) organic polymers, such as polydextrose or, which is most widely used, polyvinylpyrrolidone (povidone).

Although most iodophors are water-soluble, their dissolution in aqueous medium is generally a lengthy operation, the iodophor tending to clump on the water's surface. This means that iodophor formulations are generally manufactured and sold in liquid (aqueous) form rather than the more convenient solid form.

It is an object of the present invention to provide a solid iodophor composition that is readily soluble in aqueous medium.

Other objects and advantages of the present invention will become apparent from the following detailed description thereof.

According to the present invention there is provided a solid iodophor composition in the form of a granulate or powder comprising a water-soluble iodophor and at least one of a urea and a sugar alcohol, the composition being readily soluble in water. In the present specification, "readily soluble in water" means that the amount of the composition that contains 0.5 g of the iodophor will dissolve in 50 ml of water, with stirring (at 100 rpm) at 25° C., within 10 minutes, preferably within 5 minutes, of mixing. The iodophor composition may be in the form of a spray-dried powder. Alternatively, the composition may simply be obtained by dry mixing or wet granulating the components.

The urea may be, for example, a water soluble alkylurea or dialkylurea. Preferably the urea is unsubstituted urea ($NH_2CONH_2$).

Preferably the sugar alcohol has a molecular weight between 90 and 550, especially between 150 and 370. Suitable sugar alcohols are mannitol, sorbitol, or which is preferred, xylitol.

The urea and/or sugar alcohol is preferably finely-divided, all of the urea and/or sugar alcohol preferably having particle sizes of 600 microns or less (30 mesh sieve). In a particularly preferred embodiment of the present composition, at least 90% (by wt) of the urea and/or sugar alcohol will have particle sizes of 250 microns or less (60 mesh).

The iodophor must be water soluble. The most suitable iodophors are complexes of iodine with non-ionic, non-detergent organic polymers, especially polydetrose iodine or, which is particularly preferred, povidone iodine.

Povidone iodine is a well known iodophor that is a highly effective germicide, providing a broad spectrum of microbiocidal action against virtually all microbes. It may be prepared by any of a number of known routes, see, for example, European Published Application Nos. 120301A and 6340A and British Pat. No. 1580596, the contents of which references are incorporated herein by reference.

Polydextrose is a nonnutritive polysaccharide, prepared by the condensation polymerisation of saccharides in the presence of polycarboxylic acid catalysts, under reduced pressure. Polydextrose is described in U.S. Pat. Nos. 3766105 and 3786794, and is available from Pfizer Inc., New York. Commercially available polydextrose polymer is a low molecular weight, water-soluble, randomly bonded polymer of glucose containing minor amounts of sorbitol end groups and citric acid residues attached to the polymer by mono- and di-ester bonds. The number average molecular weight of this commercially available material is 1,500, ranging from about 160 to about 20,000.

When polydextrose polymer is combined with elemental iodine, preferably in the presence of an alkali metal iodide, the resultant polydextrose iodine complex is formed. This complex is a tan-to-amber coloured product which melts between 90° C. and 130° C. to form a red liquid. Polydextrose iodine powder is highly soluble in water and at room temperature results in a reddish brown coloured aqueous solution. Poyldextrose iodine is described in European patent application No. 172984A, the contents of which reference are incorporated herein by reference.

The water-soluble idoophor is preferably finely-divided having particle sizes of 600 microns or less (30 mesh sieve). In a particularly preferred embodiment of the present composition, at least 90% (by wt) of the iodophor will have particle sizes of 250 microns or less (60 mesh).

The amount of iodine incorporated in the iodophors used in the present composition will be determined by, amongst other factors, the amount of iodophor present in the composition and the required antibacterial strength of the composition. Preferably, iodine will constitute between 1 and 20% (by wt), especially between 2 and 15% (by wt) of the iodophor dry weight.

The concentration of the iodophur in the present composition will depend on the antibacterial strength required which will be determined by the proposed use of the composition. In addition, iodophor concentration will be determined by, amongst other factors, the iodophor employed, the propensity of the iodophor to cause irritation the amount of iodine in the iodophor and the solubility of the iodophor in water.

Thus, the composition preferably contains enough iodophor to afford a concentration of available (titratable) iodine within the composition of between 0.1 and 4.5% (by wt), especially between 0.1 and 2% (by wt), most especially between 0.2 and 1.5% (by wt).

Thus, a composition employing povidone iodine, with 10% (by wt) available iodine, as the iodophor, would preferably contain between 1 and 45%, especially between 1 and 20%, most especially between 2 and 15% (by wt) of povidone iodine.

The present composition may also contain selected pharmaceutical excipients that will facilitate its dissolution in aqueous medium. Suitable materials include (a) sugars, such as a monosaccharide, e.g. the hexoses, glucose, fructose, galactose and mannose, or, which is particularly preferred, the disaccharides, sucrose and lactose, and (b) buffering materials, such as alkali metal phosphates (e.g. disodium phosphate) and carboxylic acids (e.g. citric acid).

In the absence of sugars, the present composition preferably contains at least 60% (by wt), especially at least 75% (by wt) of a urea or a sugar alcohol. In the presence of a sugar, the present composition preferably contains between 5 and 90% (by wt) of the sugar and between 90 and 5% (by wt) of the urea or the sugar alcohol the total weight of the sugar/urea/sugar alcohol being at least 60% (by wt), especially at least 75% (by wt) of the composition.

Preferably the weight ratio of water soluble iodophor to urea/sugar alcohol/sugar in the present composition is between 1 to 1.5 and 1 to 100.

The present composition is in the form of a granulate or a powder. Its ability to be rapidly dissolved in water allows iodophors to be supplied (to hospitals, doctors, pharmacies) in a convenient, solid form rather, as has previously been the case, in a less convenient, liquid form. Once supplied, the present composition may be used to form iodophor solutions, for use as antiseptic solutions, scrubs, gargles, etc. Alternatively the present composition may be used in its solid, especially powdered, form for the treatment of wounds.

In a further aspect of the present invention, there is provided a process for the preparation of a solid iodophor composition in the form of a powder comprising spraying at least one of a urea and a sugar alcohol in a fluidised bed granulator with a solution of a water-soluble iodophor in a solvent comprising water and an alkyl alcohol having a boiling point, at 760 mm Hg, below 100° C.

Any alkyl alcohol having a boiling point, at 760 mm Hg, below 100° C., may be employed in the present process. Alkyl alcohols, such as methanol, ethanol and isopropanol, having a boiling point (at 760 mm Hg) below 90° C. are preferred, with ethanol being particularly preferred.

Any ratio of alcohol to water in the present solvent that produces a powder by the present process may be employed. The ratio is chosen so that the evaporation of the solvent is neither too slow nor too rapid. If the evaporation is too slow it would lead to sticky products, whereas, if it were too rapid, it would lead to non-homogenous products. The present inventors have found that the most effective solvent for use in the preent process contains between 70 and 85% (v/v) alkyl alcohol and between 30% and 15% (v/v) water, especially between 75% and 80% (v/v) alkyl alcohol and between 25% and 20% (v/v) water.

It is an important feature of the present process that the pH of the subsequent solid iodophor composition may be adjusted to a value that is well tolerated physiologically. Well tolerated powders will produce 50% (w/v) aqueous solutions that have a pH between 3.0 and 7.0, especially between 4.0 and 6.0.

This adjustment may be effected by the addition of a base to the iodophor solution prior to spraying. In a particularly preferred embodiment of this process, a solution of povidone iodine in aqueous ethyl alcohol is neutralised with sodium hydroxide solution. In this embodiment, once the process is complete, a 50% (w/v) aqueous solution of the subsequent povidone iodine powder has a pH between 4.5 and 5.0.

Alternatively, a solid iodophor composition according to this invention in the form of a powder may be prepared by mixing a water soluble iodophor with at least one of a urea and a sugar alcohol to form a homogenous powder.

The granulate may be prepared, by contrast, by mixing an iodophor and, at least one of a urea and a sugar alcohol in water to form a wet mass, sieving the wet mass through a sieve and drying the sieved material. Preferably the sieve has a mesh size between 8 and 30.

The present composition and methods for preparation of the composition will now be described by way of Example only.

EXAMPLE 1

Finely divided sucrose (6.5 kg) was brought into a fluidised bed granulator at 40° C. The sucrose was then sprayed with an aqueous solution (1.5 liter) containing disodium phosphate (52.2 g) and citric acid (21.6 g). The powder obtained was mixed with urea (1.35 kg), previously sieved through a 30 mesh screen.

Povidone iodine (1.08 kg) was dissolved in a mixture of 96% ethanol (4.68 kg) and distilled water (1.4 g). This solution was neutralised with 4N sodium hydroxide solution (to pH7) and then sprayed onto the sucrose/urea powder in the fluidised bed granulator at 40° C.

The powder obtained was sieved through a 23 mesh screen to give a yellowbrown, free-flowing, homogeneous powder.

EXAMPLE 2

Finely divided sorbitol (7.5 kg) was brought into a fluidised bed granulator at 40° C. Povidone iodine (1 kg) was dissolved in a mixture of 96% ethanol (b 4.68 kg) and distilled water (1.4 kg). This solution was neutralised with 4N sodium hydroxide solution and then sprayed onto the sorbitol powder.

The powder obtained was sieved through a 0.6 mm screen to remove any coarse particles. The final product was a yellow-brown, free-flowing, homogeneous powder.

Dissolution Studies

The dissolution rates of a number of compositions, containing varying quantities of urea and sucrose, were investigated in aqueous medium at 25° C.

Each 5 g sample was added to 50 ml of purified water stirred at 100 rpm. The amount dissolved was measured by a spectrophotometric procedure (absorption at 420 nm). Results are given in Table 1.

TABLE 1

| Example | PVPI (% by wt) | Urea (% by wt) | Sucrose (% by wt) | Dissolution Time |
|---|---|---|---|---|
| 3 | 10 | 15 | 75 | 2 min |
| 4 | 10 | 10 | 80 | 3.5 min |
| 5 | 10 | 5 | 85 | 5 min |
| 6 | 10 | 90 | — | 1.5 min |

EXAMPLE 7

Finely divided xylitol (4.5 g) was ground with povidone iodine (0.5 g) to form an intimate mixture.

The dissolution time of this composition was determined in 50 ml distilled water at 25° C. (±0.5° C.) in a 100 ml flat-bottomed beaker. The water was stirred at 100 rpm with a 25 mm magnetic stirrer bar. The amount dissolved was measured by a spectrophotometric procedure (absorption at 420 nm). Results are given in Table 2.

Povidone iodine and xylitol were each observed to have considerable static charges. When mixed, there was apparently no net charge. Neutralisation of the static charge on PVPI powder greatly facilitates the handling of solid PVPI. Futhermore, the opposite charges on PVPI and xylitol will help maintain the homogeneity of this mixture.

EXAMPLE 8

The procedure of Example 7 was followed except that finely divided sorbitol (4.5 g) replaced xylitol. Results of the dissolution of this mixture are given in Table 2.

EXAMPLE 9

The procedure of Example 7 was followed except that finely divided mannitol (4.5 g) replaced xylitol. Results of the dissolution of this mixture are given in Table 2.

TABLE 2

| Example | Sugar Alcohol | Time |
| --- | --- | --- |
| 0.5 g PVPI (Comparative) | | 45 min |
| 7 | Xylitol | 1.0 min |
| 8 | Sorbitol | 1.2 min |
| 9 | Mannitol | 1.7 min |

EXAMPLE 10

Finely divided xylitol (0.75 g) was ground with povidone iodine (0.5 g) to form an intimate mixture.

The dissolution time of this composition was determined as described in Example 7. Results are given in Table 3.

EXAMPLE 11

Finely divided xylitol (b 0.667 g) was ground with povidone iodine (0.5 g) to form an intimate mixture.

The dissolution time of this composition was determined as described in Example 7. Results are given in Table 3.

EXAMPLE 12

Finely divided xylitol (4.0 g) was ground with povidone iodine (1.0 g) to form an intimate mixture.

The dissolution time of this composition was determined as described in Example 7. Results are given in Table 3.

EXAMPLE 13

Finely divided xylitol (3.5 g) was ground with povidone iodine (1.5 g) to form an intimate mixture.

The dissolution time of this composition was determined as described in Example 7. Results are given in Table 3.

EXAMPLE 14

Finely divided xylitol (3.0 g) was ground with povidone iodine (2.0 g) to form an intimate mixture.

The dissolution time of this composition was determined as described in Example 7. Results are given in Table 3.

TABLE 3

| Example | Amount of PVPI | Amount of Xylitol | Dissolution Time |
| --- | --- | --- | --- |
| Comparative | 0.5 g | — | 45.0 min |
| 10 | 0.5 g | 0.75 g | 2.5 min |
| 11 | 0.5 g | 0.667 g | 9.5 min |
| 12 | 1.0 g | 4.0 g | 2.5 min |
| 13 | 1.5 g | 3.5 g | 3.5 min |
| 14 | 2.0 g | 3.0 g | 4.0 min |

I claim:

1. A solid iodophor composition in granular or powdered form, said composition being readily soluble in water and comprising a water soluble iodophor and a solubilizing agent selected from the group consisting of a urea and a sugar alcohol, said solubilizing agent having a particle size of up to 600 microns.

2. A composition according to claim 1, wherein said solubilizing agent is urea ($H_2NCONH_2$).

3. A composition according to claim 1 wherein said sugar alcohol is selected from the group consisting of mannitol, sorbitol and xylitol.

4. A composition according to claim 3 wherein said sugar alcohol is xylitol.

5. A composition according to claim 1 wherein said water-soluble iodophor is povidone iodine.

6. A composition according to claim 1 wherein at least 90% of said solubilizing agent has a particle size of 250 microns or less.

7. A composition according to claim 1, wherein the composition contains at least 60% (by wt) of said solubilizing agent.

8. A composition according to claim 7 wherein the composition contains at least 75% (by wt) of said solubilizing agent.

9. A composition according to claim 1, and also containing at least one sugar.

10. A composition according to claim 9 wherein said sugar is selected from the group consisting of sucrose and lactose.

11. A composition according to claim 9 wherein the composition contains between 5% and 90% (by wt) of said sugar and between 90% and 5% (by wt) of said solubilizing agent, the total weight of the sugar and solubilizing agent being at least 60% (by wt) of the composition.

12. A composition according to claim 11 wherein the total weight of the sugar and solubilizing agent is at least 75% (by wt) of the composition.

13. A process for the preparation of a solid iodophor composition according to claim 1 in the form of a powder, which comprises spraying said urea or sugar alcohol in a fluidised bed granulator with a solution of a water soluble iodophor in a solvent comprising water and an alkyl alcohol having a boiling point, at 760 mm Hg, below 100° C.

14. A process according to claim 13 wherein the solvent comprises between 70% and 85% (v/v) alkyl alcohol and between 30% and 15% (v/v) water.

15. A solid iodophor composition in granular or powdered form, said composition being readily soluble in water and comprising a water soluble iodophor and a solubilizing agent selected from the group consisting of a urea and a sugar alcohol, wherein 90–100% by weight of said solubilizing agent, has a particle size of up to 250 microns.

* * * * *